US00PP33478P2

(12) United States Plant Patent
Church

(10) Patent No.: US PP33,478 P2
(45) Date of Patent: Sep. 14, 2021

(54) ***MAGNOLIA* PLANT NAMED 'GCCHU2008'**

(50) Latin Name: *Magnolia laevifolia*
Varietal Denomination: GCCHU2008

(71) Applicant: Glyn Church, New Plymouth (NZ)

(72) Inventor: Glyn Church, New Plymouth (NZ)

( * ) Notice: Subject to any disclaimer, the term of this patent is extended or adjusted under 35 U.S.C. 154(b) by 0 days.

(21) Appl. No.: 17/095,901

(22) Filed: Nov. 12, 2020

(51) Int. Cl.
*A01H 5/02* (2018.01)
*A01H 6/00* (2018.01)

(52) U.S. Cl.
USPC ..... Plt./223
CPC ..... *A01H 6/00* (2018.05)

(58) Field of Classification Search
USPC ..... Plt./223
CPC ..... A01H 6/00
See application file for complete search history.

(56) References Cited

PUBLICATIONS

UPOV hit on *Magnolia* plant named, 'GCCHU2008', QZ PBR 20202180, filed Sep. 17, 2020.*

* cited by examiner

*Primary Examiner* — Anne Marie Grunberg
(74) *Attorney, Agent, or Firm* — Penny J. Aguirre

(57) ABSTRACT

A new cultivar of *Magnolia* plant named 'GCCHU2008' that is characterized by its good branching habit that readily produces vegetative buds, its velvety flower buds that develop into cup-shaped flowers that are white in color in the spring, its very floriferous blooming habit with fragrant flowers, its fine, willow-like foliage that is green in color, its dwarf and rounded plant habit, and its suitability for growing in small gardens and in 3-liter containers.

2 Drawing Sheets

Botanical classification: *Magnolia laevifolia.*
Variety denomination: 'GCCHU2008'.

BACKGROUND OF THE INVENTION

The present invention relates to a new and distinct cultivar of *Magnolia laevifolia*. The new cultivar will be referred to hereafter by its cultivar name, 'GCCHU2008'. 'GCCHU2008' is a new cultivar of *Magnolia* grown for use as a landscape shrub.

The New cultivar arose from an ongoing breeding program in Taranaki, New Zealand. The objectives of the breeding program were to develop new cultivars of *Magnolia* with dwarf and well-branched plant habits, floriferous blooming habits, and large flowers. 'GCCHU2008' originated from a cross made in in 1980 between *Magnolia laevifolia* 'Gail's Favourite' (not patented) as the female parent and an unnamed and unpatented plant of *Magnolia laevifolia* (not patented) as the male parent. 'GCCHU2008' was selected as a single unique plant in 2001 from amongst the resulting seedlings.

Asexual propagation of the new cultivar was first accomplished by semi-hardwood stem cuttings by the Inventor in Taranaki, New Zealand in 2001. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GCCHU2008' as a new and unique cultivar of *Magnolia.*

1. 'GCCHU2008' exhibits good branching habit and readily produces vegetative buds.
2. 'GCCHU2008' exhibits velvety flower buds that develop into cup-shaped flowers that are white in color in the spring.
3. 'GCCHU2008' exhibits a very floriferous blooming habit with fragrant flowers.
4. 'GCCHU2008' exhibits fine, willow-like foliage that is green in color.
5. 'GCCHU2008' exhibits a dwarf and rounded plant habit.
6. 'GCCHU2008' exhibits suitability for growing in small gardens and in 3-liter containers.

The female parent of 'GCCHU2008' differs from 'GCCHU2008' in having flowers that are smaller in size and a larger plant size. The pollen parent of 'GCCHU2008' is similar to 'GCCHU2008' in having large flowers but differs from 'GCCHU2008' in having a larger plant size. 'GCCHU2008' can also be compared to the *Magnolia* cultivar 'Dashner Denning' (not patented). 'Dashner Denning' is similar to 'GCCHU2008' in having a dwarf plant habit. 'Dashner Denning' differs from 'GCCHU2008' in having a plant habit that is more prostrate, less rounded and less compact.

BRIEF DESCRIPTION OF THE DRAWINGS

The accompanying colored photographs illustrate the overall appearance and distinct characteristics of the new *Magnolia*. The photographs were taken of a 4-year-old plant of the new cultivar as grown outdoors in 40-cm containers in Boskoop, the Netherlands.

The photograph in FIG. 1 provides a side-view of 'GCCHU2008' in bloom.

Figure 1:
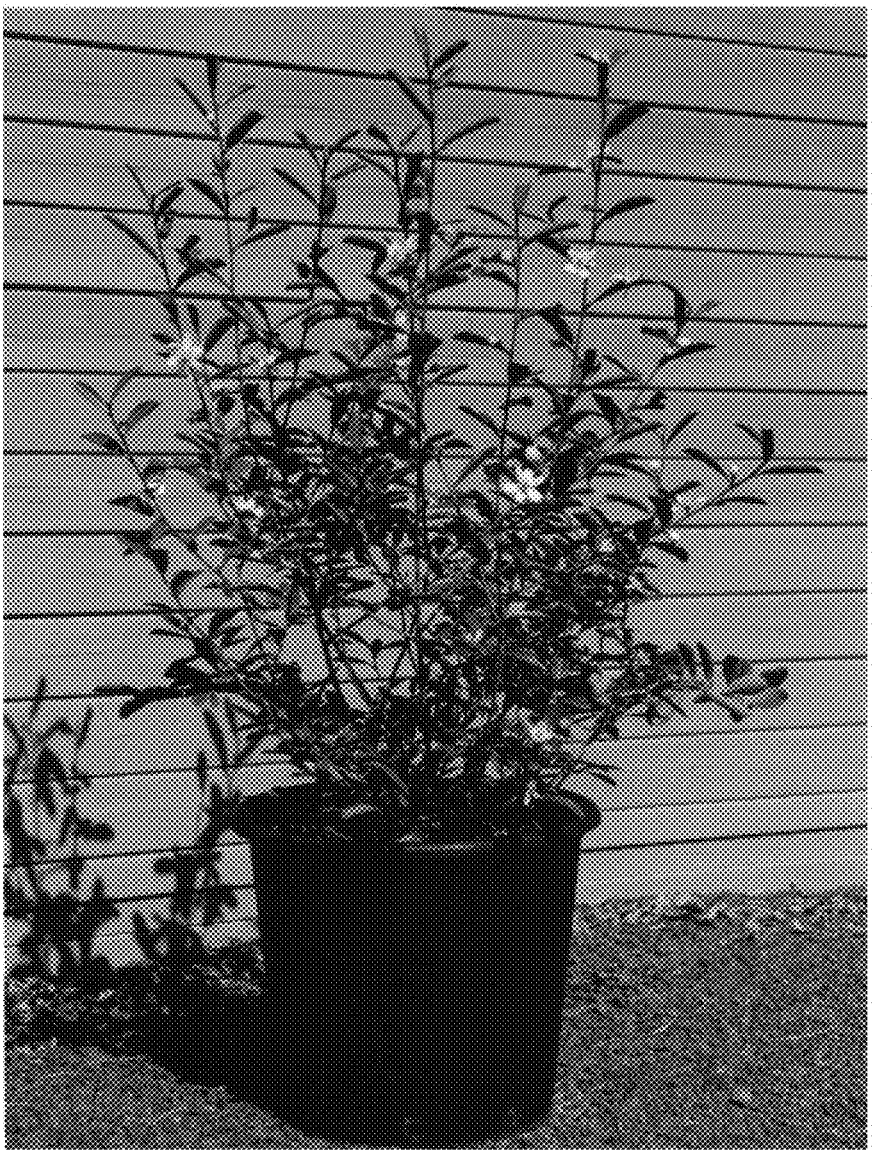
Figure 2:
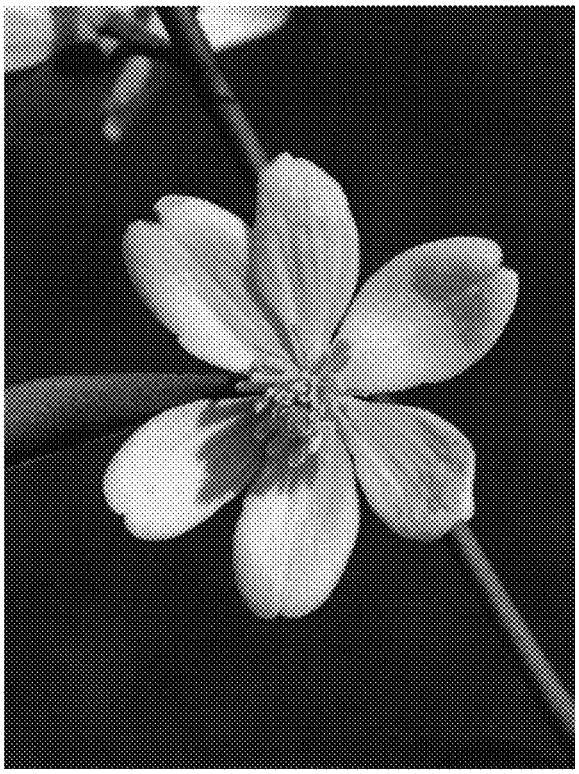

The photograph in FIG. 2 provides a close-up view of a flower of 'GCCHU2008'.

Figure 3:
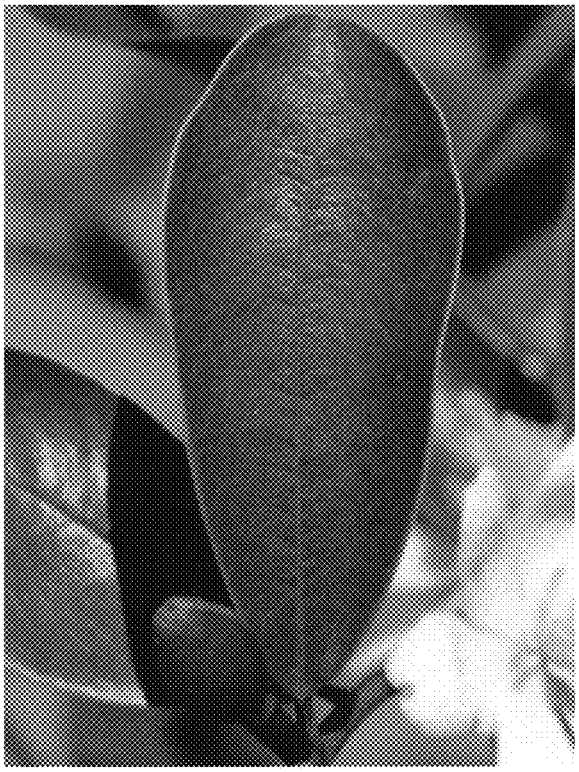

The photograph in FIG. 3 provides a close-up view of the foliage of 'GCCHU2008'.

The colors in the photographs are as close as possible with the photographic and printing technology utilized and the color values cited in the detailed botanical description accurately describe the colors of the new *Magnolia*.

DETAILED BOTANICAL DESCRIPTION

The following is a detailed description of 4-year-old plants of the new cultivar as grown outdoors in 40-cm containers in Boskoop, the Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—March in The Netherlands.

*Plant type*.—Evergreen shrub.

*Plant habit*.—Broadly ovate to spherical, broadly spreading and upright.

*Height and spread*.—Average of 70 cm in height and spread in the landscape as a mature plant.

*Diseases and pests*.—Strong resistance to fungal leaf spot cause by *Pestalotiopsis* sp. and bacterial leaf spot caused by *Xanthomonas* sp. has been observed, no susceptibility or resistance to pests has been observed.

*Propagation*.—Stem cuttings.

*Growth rate*.—Moderate.

*Root description*.—Fleshy and fibrous.

*Root development*.—Root initiation takes 6 to 8 weeks and will finish after 1.5 years in a C3 container in The Netherlands.

Branch description:

*Branch shape*.—Rounded.

*Branch color*.—Young; 146C, mature; ranging between 138B and 147B to 147C.

*Branch aspect*.—Held in an average angle of 45° (varying between 35° and 55°).

*Branch surface*.—Matte, densely covered with short soft pubescent hairs, an average of 0.4 mm in length, 166B in color.

*Branching*.—An average of 8 primary branches, 24 lateral branches.

*Internode length*.—Average of 4.4 cm.

*Branch size*.—Average of 53.4 cm in length, 4 mm in diameter.

Foliage description:

*Leaf type*.—Simple.

*Leaf shape*.—Obovate to nearly oblong.

*Leaf apex*.—Retuse.

*Leaf base*.—Obtuse.

*Leaf arrangement*.—Alternate.

*Leaf margins*.—Entire, very slightly and coarsely undulate.

*Leaf venation*.—Pinnate, upper surface color 197A, lower surface color 152D.

*Leaf color*.—Young upper surface; 152C, young lower surface 152D, mature upper surface NN137A, mature lower surface 148B.

*Leaf number*.—An average of 13 per branch.

*Leaf surface*.—Upper surface; moderately glossy and moderately covered with very short, soft adpressed hairs an average of 0.2 mm and matches leaf surface color, lower surface; matte and densely covered with very short, soft adpressed hairs an average of 0.2 mm, matches leaf surface color.

*Petioles*.—An average of 7 mm in length and 2.25 mm in diameter, strong, both surfaces 146D in color, both surfaces matte and densely covered with very short, soft adpressed hairs an average of 0.3 mm in length and 166B in color.

Inflorescence description:

*Inflorescence type*.—Solitary, placed axillary and terminal.

*Flower number*.—An average of 50 per plant.

*Flower fragrance*.—Moderately strong, sweet and acidic, pleasant *Magnolia* fragrance.

*Flower longevity*.—An average of 10 days, self-cleaning.

*Flower type*.—Rotate, single, freely flowering.

*Flower aspect*.—Outward.

*Flower size*.—An average of 5.7 cm in diameter and 3.4 cm in depth.

*Flower buds*.—Average of 200 per plant, obovate in shape, an average of 1.6 cm in length and 1.1 cm in width, surface is smooth, glabrous and matte, color; 150D, changing to 149C to 150C at the base.

*Floral bracts*.—Flower bud is covered with a single bract, dropped about 2 weeks before flower opens, reniform in shape, folded around flower bud, average of 1.1 cm in length, 1.4 cm in width, emarginate apex, broadly cuneate base, color; upper surface between 199A and 199B, lower surface 166C, surfaces; upper surface smooth and glabrous, lower surface is very densely covered with very short, soft hairs an average of 0.3 mm in length and 166C in color.

*Tepals*.—6 per flower (occasionally 7 to s8), arranged in a single whorl, rotate, slightly to moderately reflexed, obovate to oblong in shape, narrowly cuneate base, shallow emarginate apex, entire margins, average of 3 cm in length, 1.6 cm in width, color; when opening upper surface 155A, changing to 145C at the base, when opening lower surface between 150D and 155A, changing to 145B at the base, when fully open upper surface 155B, changing to 150D at the base, when fully open lower surface 155B to 155C, changing to 150C to 150D at the base, surfaces; upper surface smooth, glabrous, moderately velvety and matte, lower surface smooth, glabrous, slightly velvety and very slightly glossy.

*Pedicels*.—Round in shape, very strong, an average of 1.3 cm in length, 2.5 mm in diameter, held in an average angle of 45° (varying between 20° and 70°), 146D in color, surface is matte and densely covered with very short, soft adpressed hairs, an average of 0.3 mm in length, 166B in color.

Reproductive organs:

*Gynoecium*.—Pistils; average of 8, 3 mm in length, clustered at the top of an elongated receptacle, receptacle; average of 1 cm in length, 1 mm in diameter, 150D in color, stigma; pointed in shape, average of 0.1 mm in length, 0.2 mm in diameter, 166B in color, style; average of 0.75 mm in length, 154D in color, ovary; 145C in color.

*Androecium*.—Stamens; average of 65, filaments; 2 mm in length and between 150D and 154D in color, anthers; basifixed, narrowly oblong in shape, an average of 6 mm in length and 1 mm in width, 154D in color, pollen is low in quantity and 161D in color.

*Fruit and seed*.—None observed to date.

It is claimed:

1. A new and distinct cultivar of *Magnolia* plant named 'GCCHU2008' as herein illustrated and described.

* * * * *